US008679527B2

(12) United States Patent  
Keiji et al.

(10) Patent No.: US 8,679,527 B2  
(45) Date of Patent: Mar. 25, 2014

(54) ANTIMICROBIAL COMPOSITIONS

(75) Inventors: Terao Keiji, Kobe (JP); Ayako Jo, Kobe (JP); Daisuke Nakata, Kobe (JP)

(73) Assignee: Manuka Health New Zealand Limited, Te Awamutu (NZ)

( * ) Notice: Subject to any disclaimer, the term of this patent is extended or adjusted under 35 U.S.C. 154(b) by 141 days.

(21) Appl. No.: 13/124,101

(22) PCT Filed: Oct. 12, 2009

(86) PCT No.: PCT/IB2009/054458  
§ 371 (c)(1),  
(2), (4) Date: Jul. 8, 2011

(87) PCT Pub. No.: WO2010/044042  
PCT Pub. Date: Apr. 22, 2010

(65) Prior Publication Data  
US 2011/0263528 A1     Oct. 27, 2011

(30) Foreign Application Priority Data

Oct. 14, 2008    (JP) ................................. 2008-265342

(51) Int. Cl.  
*A61K 31/11*      (2006.01)  
*A61K 31/121*      (2006.01)  
*A61K 31/724*      (2006.01)  
*A61K 47/40*      (2006.01)  
*A61L 15/14*      (2006.01)  
*A61L 15/28*      (2006.01)  
*A61P 17/02*      (2006.01)  
*A61P 31/00*      (2006.01)  
*A23L 1/08*      (2006.01)

(52) U.S. Cl.  
USPC .............. 424/447; 424/539; 514/58; 514/675

(58) Field of Classification Search  
None  
See application file for complete search history.

(56) References Cited

U.S. PATENT DOCUMENTS

| | | | | |
|---|---|---|---|---|
| 4,529,608 | A * | 7/1985 | Szejtli et al. .................... | 426/96 |
| 2004/0127826 | A1 * | 7/2004 | Caskey ........................... | 602/41 |

FOREIGN PATENT DOCUMENTS

| | | | |
|---|---|---|---|
| NZ | 502158 | * | 5/2002 |
| WO | WO 02/09782 | * | 2/2002 |
| WO | WO 2005/053431 | * | 6/2005 |
| WO | 2006/121350 | | 11/2006 |

OTHER PUBLICATIONS

Nemet, I. et al "Methylglyoxal in food and living organisms" Mol. Nutr. Food Res. (2006) vol. 50, pp. 1105-1117.*  
International Search Report for International Application PCT/IB2009/054458, issued Dec. 17, 2009.

Abbott, W.S. (1925) "A Method of Computing the Effectiveness of an Insecticide," J Econ Entomol 18:265-267.  
Al Somal et al. (1994) "Susceptibility of *Helicobacter pylon* to the antibacterial activity of manuka honey" Journal of the Royal Society of Medicine 87:9-12.  
Anis et al. (1982) "Susceptibility of Different Populations of Glasshouse Whitefly *Trialeurodes vaporariorum* (Westwood) to a Range of Chemical Insecticides," Faculty of General Agriculture University College of Dublin, Research Report 1980-1981, p. 55.  
Elhag et al. (1983) "Resistance of Greenhouse Whitefly (Homoptera: Aleyrodidae) to Insecticides in Selected Ohio Greenhouses," J Econ Entomol 76(4):945-948.  
Gorman et al. (2000) "Status of Pesticide Resistance in UK Populations of Glasshouse Whitefly, *Trialeurodes vaporariorum*, and the Two-Spotted Spider Mite, *Tetranychus urticae*," The BCPC Conference: Pests and Diseases 1:459-464.  
Grossman, J. (Apr. 1994) "Onion Thrips," IPM Practitioner 16(4):12-13.  
Hall, R. A. (1980) "Control of Aphids by the Fungus, *Verticillium lecanii*: Effect of Spore Concentration," Ent. Exp. & Appl. 27:1-5. *Ned. Entomol. Ver. Amsterdam.*  
Hommes, M. (1986) "Insecticide Resistance in Greenhouse Whitefly (*Trialeurodes vaporariorum*, Westw.) to Synthetic Pyrethroids," Mitteilungen aus der Biologischen Bundesanstalt fur Land-und Forstwirtschaft 232:376-377 (German language).  
Martin et al. (1994) "Confirmation of a Pesticide-Resistant Strain of Western Flower Thrips in New Zealand," Proc 47th N.Z. Plant Protection Conf, pp. 144-148.  
Martin, N.A. (1996) "Whitefly Insecticide Resistance Management Strategy," In: Bourdot, G.W., Suckling, D.M. (eds). Pesticide Resistance: Prevention & Management., New Zealand Plant Protection Society, Lincoln, NZ, pp. 194-203.  
Marvic et al. (2008) "Identification and quantification of methylglyoxal as the dominant antibacterial constituent of Manuka (*Leptospermum scoparium*) honeys from New Zealand" Molecular Nutrition and Food Research 52(4):483-489.  
Murad et al. (2007) "Screening and Secretomic Analysis of Enthomopatogenic *Beauveria bassiana* Isolates in Response to Cowpea Weevil (*Callosobruchus maculatus*) Exoskeleton," Comparative Biochemistry and Physiology, Part C, 145:333-338.  
Purvis, S. (May 2002) "Are KCT developing resistance to chlorpyrifos," Talking Thrips *in Citrus* Issue 1, p. 2.  
Santoro et al. (2008) "Selection of *Beauveria bassiana* Isolates to Control *Alphitobius diaperinus*," Journal of Invertebrate Pathology 97:83-90.  
Sassá et al. (Nov. 1, 2009) "Genetic Variation in a Chitinase Gene of *Beauveria bassiana*: Lack of Association Between Enzyme Activity and Virulence Against *Hypothenemus hamper*", Journal of Entomology 6(1):35-41.  
Visavadia et al. (2008) "Manuka honey dressing: An effective treatment for chronic wound infections", Br J Oral Maxillofac Surg 46:55-56.  
Wardlow, L.R. (1985) "Pyrethroid Resistance in Glasshouse Whitefly (*Trialeurodes vaporariorum*, Westw.)," Mededelingen van de Faculteit Landbouwwetenschappen, Rijksuniversiteit, Gent 50(2b):555-557.

* cited by examiner

*Primary Examiner* — Leigh Maier  
(74) *Attorney, Agent, or Firm* — Lathrop & Gage LLP

(57) ABSTRACT

This invention provides antimicrobial compositions containing methylglyoxal and material with methylglyoxal contained (such as manuka honey). The antimicrobial activity of methylglyoxal, or material with a methylglyoxal presence, is maintained and/or enhanced by mixing methylglyoxal or material with a methylglyoxal presence with cyclodextrin. Methods of preparing such compositions, including powder composition, and methods of using such compositions are also provided.

11 Claims, 3 Drawing Sheets

ANTIMICROBIAL COMPOSITIONS

CROSS-REFERENCE TO RELATED APPLICATIONS

This application is a National Stage Application filed under 35 U.S.C. §371 of PCT Application No. PCT/IB2009/054458, filed on Oct. 12, 2009 and published in English on Apr. 22, 2010 as WO 2010/044042, which claims priority to Japanese Patent Application 2008-265342, filed on Oct. 14, 2008, all of which are incorporated by reference in their entireties to the extent there is no inconsistency with the present disclosure.

FIELD OF INVENTION

This invention relates to antimicrobial compositions. In particular, this invention relates to antimicrobial compositions containing methylglyoxal and cyclodextrin, including antimicrobial compositions containing one or more materials with a methylglyoxal presence and one or more materials with a cyclodextrin presence. Particularly contemplated are antimicrobial compositions comprising manuka honey as the one or more materials with a methylglyoxal presence, and cyclodextrin.

BACKGROUND OF THE INVENTION

Manuka honey is the natural honey which is produced by bees which gather nectar from manuka bush (*Leptospermum scoparium*) growing throughout New Zealand. This species is also found in Australia, where the honey is known under different names, such as Jellybush honey. It contains constituent actives that exhibit stability in the presence of heat, light, gastric juice, enzyme, etc. It has been reported that manuka honey inhibits the growth of *Staphylococcus aureus, Helicobacter pylori*, and *Escherichia coli*, etc. J. Roy. Soc. Med. 1994; 87:9-12.

Identification of the antimicrobial constituent(s) present in manuka honey has been difficult, and it has been referred to as "Unique Manuka Factor" or non-peroxide activity (NPA). This is the anti-bacterial activity which exists in manuka honey in addition to the unstable anti-bacterial activity reported in all honeys that is believed to be due to hydrogen peroxide. Recently, it has been reported that methylglyoxal is the dominant manuka-specific antibacterial constituent, Mol. Nutr. Food Res. 2008 April; 52(4) 483-489.

Methylglyoxal has been suggested as an effective antimicrobial ingredient of water-soluble detachment solution for washing or industrial use disinfectants comprising food additives or internal agent ingredients, Unexamined publication JP2008-7408 and Unexamined publication JPH8-239693.

It has been reported that naturally produced methylglyoxal is contained in dairy products and fermented products like beer and wine at the concentration of 3 to 11 mg/kg, in roasted coffee at the concentration of 23 to 47 mg/kg, and in manuka honey at concentrations of 38 to 761 mg/kg.

Therefore, with this high antimicrobial activity, there has been an expectation that manuka honey can be used for the treatment of skin and wound infections caused by *Staphylococcus aureus* by topical application, or for the treatment of duodenal ulcer, gastric ulcer, gastric cancer and so on caused by *Helicobacter pylori*, through ingestion. However, for manuka honey to be effective, frequent application or ingestion is necessary. For these and other applications it would be desirable to have products and compositions in which the antimicrobial activity is maintained, preferably for long durations.

Accordingly, there is a need for antimicrobial compositions, including those suitable for use in the treatment of a variety of diseases and disorders in which microbial activity is associated or implicated, and those suitable for use in controlling microbial populations, which are able to support the maintenance of antimicrobial activity or augment antimicrobial activity.

It is an object of the present invention to provide antimicrobial compositions, including stable antimicrobial compositions, or to at least provide the public with a useful choice.

SUMMARY OF THE INVENTION

Accordingly, in a first aspect the invention provides an antimicrobial composition comprising methylglyoxal and cyclodextrin.

In one embodiment, the antimicrobial composition comprises one or more materials comprising methylglyoxal.

In one embodiment, the material comprising methylglyoxal is manuka honey.

In one embodiment, the manuka honey has a methylglyoxal concentration of greater than about 30 mg/kg, than about 38 mg/kg, than about 40 mg/kg, about 50 mg/kg, about 60 mg/kg, about 70 mg/kg, about 80 mg/kg, about 90 mg/kg, about 100 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg, about 750 mg/kg, about 800 mg/kg, about 850 mg/kg, about 900 mg/kg, about 950 mg/kg, greater than about 1000 mg/kg, greater than about 1100 mg/kg, greater than about 1200 mg/kg, greater than about 1300 mg/kg, greater than about 1400 mg/kg, greater than about 1500 mg/kg, greater than about 1600 mg/kg, greater than about 1700 mg/kg, greater than about 1800 mg/kg, greater than about 1900 mg/kg, or about 2000 mg/kg.

In one embodiment, the manuka honey has a NPA rating greater than 10, than 15, than 20, than 25, 26, 27, 28, 29, 30, than 31, 32, 33, 34, or greater than 35.

In various embodiments, the cyclodextrin is alpha-cyclodextrin, or the cyclodextrin is gamma-cyclodextrin, or the cyclodextrin is present as a combination of alpha-cyclodextrin and gamma-cyclodextrin.

In one embodiment, the cyclodextrin is chemically-modified cyclodextrin.

In one embodiment, the composition comprises from about 10.0% wt to about 99.0% wt manuka honey.

In various embodiments, the composition comprises from about 0.003% wt to about 0.2% wt methylglyoxal, from about 0.003% wt to about 0.15% wt methylglyoxal, from about 0.006% wt to about 0.15% wt methylglyoxal, from about 0.01% wt to about 0.15% wt, from about 0.02% wt to about 0.15% wt, from about 0.03% wt to about 0.15% wt, from about 0.04% wt to about 0.15% wt, from about 0.05% wt to about 0.15% wt, from about 0.06% wt to about 0.15% wt, from about 0.07% wt to about 0.15% wt, from about 0.08% wt to about 0.15% wt, or from about 0.09% wt to about 0.15% wt methylglyoxal.

In one embodiment, the methylglyoxal content is within the range of 0.006% wt to 0.079% wt per antimicrobial composition.

In one embodiment, the composition is a consumer good.

In one embodiment the composition is a food, drink, food additive, drink additive, dietary supplement, nutritional product, medical food, nutraceutical, medicament or pharmaceutical.

In various embodiments, the composition may be formulated for oral, topical, or parenteral administration.

In one embodiment, the composition comprises one or more additional antimicrobial agents.

In one embodiment, the composition is a pharmaceutical composition.

In one embodiment, the composition is or is present in a medical device or a medical supply, including disinfectants, cleaning agents, and surgical wipes, bandages, dressings, and the like.

In one embodiment, the composition is an industrial product, including industrial solutions such as cleaning or descaling solutions.

In a second aspect the invention provides an antimicrobial composition comprising manuka honey and cyclodextrin.

In another aspect, the present invention provides a method of preparing a composition comprising methylglyoxal and cyclodextrin, the method comprising admixing methylglyoxal, or a material comprising methylglyoxal, or both, with cyclodextrin or a material comprising cyclodextrin, or both.

In one embodiment, the admixing is of a powderized material with a methylglyoxal presence with cyclodextrin or a material comprising cyclodextrin, or both.

In one embodiment, the admixing is of powderised manuka honey with cyclodextrin.

In one embodiment, the method comprises the preliminary step of drying manuka honey prior to or during powderising, such as by lyophilisation, spray-drying, de-hydration, freeze-drying, etc.

In another embodiment, the method comprises the additional step of drying the admixture, such as by lyophilisation, spray-drying, de-hydration, freeze-drying, etc.

In one embodiment, the method comprises the further step of powderising the dried admixture.

In one embodiment, the method comprises the further step of granulating the dried admixture, or of granulating the powderised admixture.

In one embodiment, the method comprises the further step of tableting or encapsulating the dried admixture, or of tableting or encapsulating the powderised admixture, or of tableting or encapsulating the granulated admixture.

In another aspect, the present invention provides a method of treating or preventing a microbial disease or disorder, the method comprising administering to a subject in need thereof a composition comprising methylglyoxal and cyclodextrin.

In another aspect, the present invention provides a method of promoting wound healing, the method comprising administering to a subject in need thereof a composition comprising methylglyoxal and cyclodextrin.

In various embodiments, the composition may be directly applied to the wound, for example by topical application to the wound or surrounding tissue, or indirectly applied to the wound, for example by application to bandages, dressings, surgical equipment, and the like.

In a further aspect the present invention provides a method for controlling one or more microbes, the method comprising contacting the one or more microbes with a composition comprising methylglyoxal and cyclodextrin.

In a further aspect the present invention provides a method for controlling one or more microbes present on or in a substrate, whether animate or inanimate, the method comprising contacting the one or more microbes or the substrate with a composition comprising methylglyoxal and cyclodextrin.

In another aspect, the present invention provides the use of methylglyoxal and cyclodextrin in the preparation of a medicament suitable for use in the treatment of a microbial disease or disorder.

In another aspect, the present invention provides the use of methylglyoxal and cyclodextrin in the preparation of a medicament suitable for use in promoting wound healing in a subject in need thereof.

In one embodiment, the use is of a mixture of methylglyoxal or a material comprising methylglyoxal, and cyclodextrin.

The present invention further provides methylglyoxal and cyclodextrin for the treatment of a microbial disease or disorder.

The present invention further provides methylglyoxal and cyclodextrin for promoting wound healing in a subject in need thereof.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention may also be said broadly to consist in the parts, elements and features referred to or indicated in the specification of the application, individually or collectively, in any or all combinations of two or more of said parts, elements or features, and where specific integers are mentioned herein that have known equivalents in the art to which the invention relates, such known equivalents are deemed to be incorporated herein as if individually set forth.

DETAILED DESCRIPTION

Figure 1:
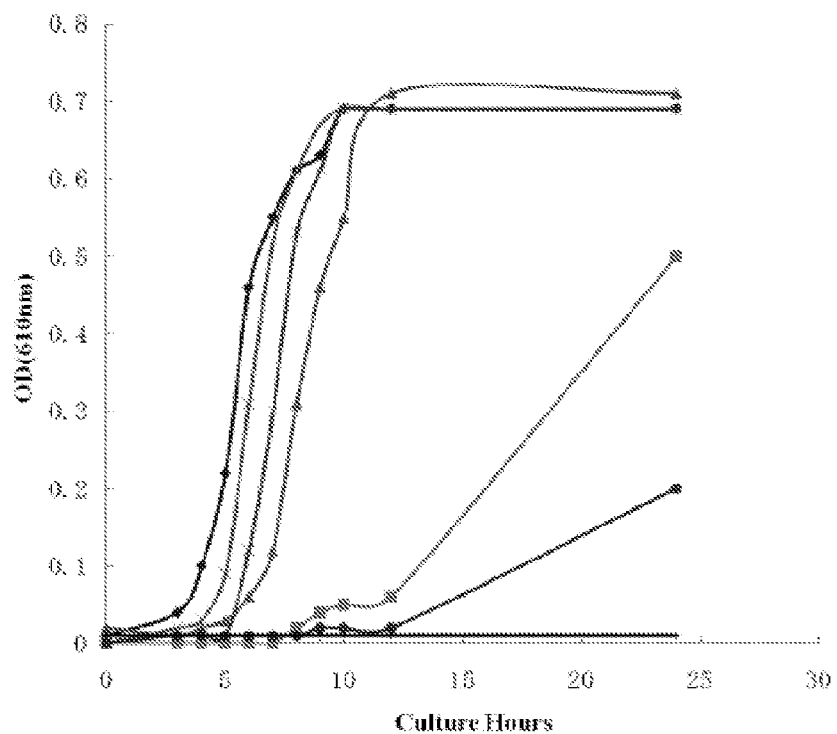
FIG. 1 Antimicrobial activity against *Staphylococcus aureus* of antimicrobial composition A are shown (Test results). ◆ Control; ■ Alpha-CD (4.0 w/v %); ▲ Manuka honey (3.27 w/v %); ><Antimicrobial mixture A (Manuka honey 0.82 w/v %, Alpha CD 1.0 w/v %); * Antimicrobial mixture A (Manuka honey 1.64 w/v %, α CD2.0 w/v %); ● Antimicrobial mixture A (Manuka honey 3.27 w/v %, Alpha-CD4, 0 w/v %); +Antimicrobial mixture A (Manuka honey 7.14 w/v %, Alpha-CD8, 7 w/v %).

The present invention is based on the finding that by admixing, for example by mixing and powderizing, materials comprising methylglyoxal and materials comprising cyclodextrin, the antimicrobial activity of the original materials is at least maintained or preferably is enhanced.

Thus, antimicrobial compositions of this invention maintain or enhance the antimicrobial activity of original methylglyoxal or materials with methylglyoxal contained.

Accordingly, provided that the antimicrobial compositions are formulated so as to be suitable for administration to a mammalian subject, for example they consist of materials that are safe to the human body, they can be used for manufacturing antimicrobial consumer goods, such as beverages, foods, and the like, as well as pharmaceutical compositions, drugs, and the like.

Since the antimicrobial activity of methylglyoxal or materials with a methylglyoxal presence is maintained in the compositions of the invention for a sustained period, the dosage or frequency of administration of the composition can be reduced, or higher efficacy provided or both.

And further, other embodiments of the invention provide antimicrobial compositions formulated for industrial use, for example, where compositions comprise industrially available or acceptable materials. Such compositions can be used for industrial products such as disinfectant for cooling water or washing water in the industry, or in various industrial processes known to those skilled in the art.

The phrases "antimicrobial compositions" or "compositions having antimicrobial activity" (used interchangeably herein) of this invention contemplate any kind of compositions, as long as the antimicrobial compositions are either antimicrobial compositions containing methylglyoxal and cyclodextrin or antimicrobial compositions containing materials with methylglyoxal contained and cyclodextrin. Compositions which maintain or enhance the original antimicrobial activity of methylglyoxal or materials with methylglyoxal contained are particularly contemplated.

The term "and/or" can mean "and" or "or".

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

The term "control" or "controlling" as used herein generally comprehends preventing, reducing, or eradicating microbial infection or inhibiting the rate and extent of such infection, or reducing the microbial population, such as a microbial population present in or on a body or structure, surface, liquid, subject, etc, wherein such prevention or reduction in the infection(s) or population(s) is statistically significant with respect to untreated infection(s) or population(s). Curative treatment is also contemplated. Preferably, such control is achieved by increased mortality amongst the microbial population.

An "effective amount" is the amount required to confer therapeutic effect. The interrelationship of dosages for animals and humans (based on milligrams per meter squared of body surface) is described by Freireich, et al. (1966). Body surface area can be approximately determined from height and weight of the subject. See, e.g., Scientific Tables, Geigy Pharmaceuticals, Ardley, N.Y., 1970, 537. Effective doses also vary, as recognized by those skilled in the art, dependent on route of administration, excipient usage, and the like.

A "medical device" as used herein includes, for example but is not limited to, any temporarily or permanently implanted device into or on a human or animal host, for example stents, balloons, prosthetic heart valves, annuloplasty rings, grafts, shunts, sewing rings having silicone or polyurethane inserts, polyester fabric encasements, stents, medical leads, orthopedic plates, catheters, pacemakers, sutures, and/or any one or more of the foregoing medical devices can include a fabric overlayer of any type, including for example a sheath, an encasement, a layer, or a coating, such that the fabric overlayer is in contact with body tissue or fluids such as blood. Alternatively, instead of the medical device including a fabric overlayer, the medical device may include a mesh, coil, wire, inflatable balloon, bead, sheet, or any other structure which is capable of being positioned or implanted at a target location, including intravascular target locations, intraluminal target locations, target locations within solid tissue, and the like. Implantation at wounds, such as surgical wounds, is particularly contemplated.

A "medical supply" and grammatical equivalents as used herein includes, for example but is not limited to, any consumable product commonly used in the practice of medicine, including for example, disinfectants, germicides, lavages, solutions, dressings, bandages, and the like.

As used herein, "microbial disease or disorder" refers to a disease or disorder caused by or exacerbated by one or more microbes, including those diseases or disorders of which one or more symptoms are caused or exacerbated by one or more microbes.

As used herein, "manuka honey" refers to a honey produced by bees from the nectar of flora of *Leptospermum* spp., in particular *Leptospermum scoparium*. Other honeys with a methylglyoxal concentration of above about 15 mg/kg, preferably above about 30 mg/kg, more preferably above about 60 mg/kg, are contemplated as suitable for use in embodiments of the present invention. This may be honey made from nectars collected by bees both from *Leptospermum* species and other species, or may be honey from species providing such a methylglyoxal content as desired. Alternatively, honeys (whether manuka or otherwise) augmented with methylglyoxal are contemplated.

When used in respect of an agent having antimicrobial activity, such as a composition of the invention or a component of a composition of the invention, the phrase "retaining antimicrobial activity" and grammatical equivalents and derivatives thereof is intended to mean that the agent still has useful antimicrobial activity. Preferably, the retained activity is at least about 35, 40, 45, 50, 55, 60, 65, 70, 75, 80, 85, 90, 95, 99 or 100% of the original activity, and useful ranges may be selected between any of these values (for example, from about 35 to about 100%, from about 50 to about 100%, from about 60 to about 100%, from about 70 to about 100%, from about 80 to about 100%, and from about 90 to about 100%). For example, to be useful in the present invention a composition should retain antimicrobial activity, that is, retain at least about 35, 40, 45, 50, 55, 60, 65, 70, 75, 80, 85, 90, 95, 99 or 100% of the antimicrobial activity of the original antimicrobial agent, for example the material comprising a methylglyoxal presence. Similarly, preferred compositions of the invention are capable of supporting the maintenance of useful antimicrobial activity of the antimicrobial agent(s) they comprise, and can be said to retain antimicrobial activity, ideally until applied using the methods contemplated herein.

When used in respect of a composition of the invention or a component of a compositon of the invention, the phrase "enhancing antimicrobial activity" and grammatical equivalents and derivatives thereof is intended to mean that when present in the composition, an equivalent amount or concentration of the antimicrobial agent has increased antimicrobial activity compared to that of the agent in the absence of the composition (such as the isolated agent). Preferably, the enhanced activity is at least about 105, 110, 115, 120, 125, 130, 135, 140, 145, 150, 155, 160, 165, 170, 175, 180, 185, 190, 195, 200%, or more of the original activity, and useful ranges may be selected between any of these values (for example, from about 35 to about 100%, from about 50 to about 100%, from about 60 to about 100%, from about 70 to about 100%, from about 80 to about 100%, and from about 90 to about 100%). In certain embodiments, compositions of the invention may exhibit enhanced antimicrobial activity, that is, exhibit at least about 105, 110, 115, 120, 125, 130, 135, 140, 145, 150, 155, 160, 165, 170, 175, 180, 185, 190, 195, 200%, or more of the antimicrobial activity of the original antimicrobial agent, for example the material comprising a methylglyoxal presence. Similarly, preferred compositions of the invention are capable of supporting the maintenance of enhanced antimicrobial activity of the antimicrobial agent(s) they comprise, and can be said to retain enhanced antimicrobial activity, ideally until applied using the methods contemplated herein. The enhanced activity (including enhanced maintenance of activity) may result from synergy amongst the various components of the compositions of the invention.

As used herein, the term "stable" when used in relation to a composition of the invention means a composition capable of supporting antimicrobial activity for preferably more than two hours, more than three hours, 6 hours, 9 hours, 12 hours, 15 hours, 18 hours, 20 hours, more than one day, preferably about two, about three, about four, preferably about five, more preferably about six days, preferably a week, two weeks, three weeks, a month, or longer. It will be appreciated that in certain embodiments, stable compositions include those which have antimicrobial activity for a period greater than does the antimicrobial agent alone.

The term "oral administration" includes oral, buccal, enteral and intra-gastric administration.

The term "parenteral administration" includes but is not limited to topical (including administration to any dermal, epidermal or mucosal surface), subcutaneous, intravenous, intraperitoneal, intramuscular and intratumoural (including any direct administration to a tumour) administration.

The term "pharmaceutically acceptable carrier" is intended to refer to a carrier including but not limited to an excipient, diluent or auxiliary that can be administered to a subject as a component of a composition of the invention. Preferred carriers do not reduce the activity of the composition and are not toxic when administered in doses sufficient to deliver an effective amount of methylglyoxl, or, when administered, of another antimicrobial agent.

The term "promote wound healing" and grammatical equivalents thereof when used with reference to the methods and compositions of the present invention contemplates improved wound healing in the presence of a composition of the invention than is or was observed in the absence of a composition of the invention. For example, a refractory wound—that is, a wound resistant to treatment or healing—exhibits improved healing following application of a composition of the present invention. Preferably, wound healing is improved by a statistically significant amount.

The term "(s)" following a noun contemplates the singular or plural form, or both.

The term "subject" is intended to refer to an animal, preferably a mammal, more preferably a mammalian companion animal or human. Preferred companion animals include cats, dogs and horses. Other mammalian subjects include an agricultural animal, including a horse, a pig, a sheep, a goat, a cow, a deer, or a fowl, or a laboratory animal, including a monkey, a rat, or a mouse.

The term "treat" and its derivatives should be interpreted in their broadest possible context. The term should not be taken to imply that a subject is treated until total recovery. Accordingly, "treat" broadly includes maintaining a subject's disease progression or symptoms at a substantially static level, increasing a subject's rate of recovery, amelioration and/or prevention of the onset of the symptoms or severity of a particular condition, or extending a patient's quality of life. The term "treat" also broadly includes the maintenance of good health for sensitive individuals and building stamina for disease prevention.

As used herein, "NPA value" means the measurement of antibacterial activity determined for a whole or sieved honey or fraction thereof determined relative to phenol equivalents in an agar plate diffusion assay.

Exemplary Uses of the Invention

The methods and compositions of the invention may be used in the treatment of microbial diseases or disorders, to promote wound healing, and to control microbial infection.

In one embodiment, the microbial disease or disorder is a bacterial disease or disorder. In one embodiment the microbial infection is a bacterial infection.

In one embodiment, the microbial disease or disorder is a fungal disease or disorder. In another embodiment, the microbial disease is a yeast disease or disorder. In one embodiment the microbial infection is a fungal infection. In one embodiment the microbial infection is a yeast infection.

In one embodiment, the microbial disease is a microbial infection of the skin, lung, buccal cavity, gastro-intestinal tract, eye, ear, sinuses, kidney, mucosal surfaces, or urinary tract.

In one embodiment, the microbial disease or disorder is a skin disease or disorder or a tissue disease or disorder, such as psoriasis, acne, ulceration, wound infection or refractory wound(s), burn(s), dermatitis, athletes foot, and eczema. For example, the microbial disease or disorder is a bacterial infection, such as a bacterial infection of a wound, including an infection of any one or more of the following bacteria: *Staphylococcus aureus*, including methicillin-resistant *Staphylococcus aureus* (MRSA), *E. coli*, or *Pseudomonas aeruginosa*.

In one embodiment, the microbial disease or disorder is a lung disease or disorder, such as chronic obstructive pulmonary disease (COPD, also referred to as chronic obstructive respiratory disease (CORD)), tuberculosis, or emphysema. For example, the microbial disease or disorder is a bacterial infection of *Mycobacteria tuberculosis*, or *Mycobacteria paratuberculosis*.

In one embodiment, the microbial disease or disorder is an oral disease or disorder, such as dental caries, gingivitis, ulcers. For example, the microbial disease or disorder is a bacterial infection of any one or more of the following bacteria: *Streptococcus salivarius, S. mitis, S. mutans, S. rattus, S. cricetus, S. sobrinus, S. ferus, S. macacae*, or *S. downei, Lactobacillus* spp., including *Lactobacillus caseii*.

In one embodiment, the microbial disease or disorder is a gastro-intestinal disease or disorder, such as gastro-enteritis, ulcers including peptic ulcers, chronic gastritis, and duodenitis. For example, the microbial disease or disorder is a bacterial infection of any one or more of the following bacteria: *Helicobacter* spp., including *H. acinonychis, H. anseris, H. aurati, H. bilis, H. bizzozeronii, H. brantae, H. canadensis, H. canis, H. cholecystus, H. cinaedi, H. cynogastricus, H. felis, H. fennelliae, H. ganmani, H. hepaticus, H. mesocricetorum, H. marmotae, H. muridarum, H. mustelae, H. pametensis, H. pullorum, H. pylori, H. rappini, H. rodentium, H. salomonis, H. trogontum, H. typhlonius, H. winghamensis, Campylobacter* spp., including *C. coli, C. concisus, C. curvus, C. fetus, C. gracilis, C. helveticus, C. hominis, C. hyointestinalis, C. insulaenigrae, C. jejuni, C. lanienae, C. lari, C. mucosalis, C. rectus, C. showae, C. sputorum, C. upsaliensis*.

In one embodiment, the microbial disease or disorder is an eye disease or disorder, such as blepharitis, conjunctivitis, keratitis including fungal keratitis. For example, the microbial disease or disorder is a microbial infection of any one or more of the following microbes: *Staphylococcus* spp., *Aspergillus fumigates, Fusarium* spp. and *Candida* spp.

In one embodiment, the microbial disease or disorder is an ear or sinus disease or disorder, such as Otitis externa, Otitis media, sinusitis including acute sinusitis, chronic sinusitis and antibiotic-refractory chronic sinusitis. For example, the microbial disease or disorder is a microbial infection of the ear or sinus, including an infection of any one or more of the following microbes: *Staphylococcus* spp. including *Staphylococcus aureus, Pseudomonas aeruginosa, Aspergillus* spp., including *Aspergillus fumigates, Streptococcus* spp. including *Streptococcus pneumonia, Haemophilus influenza, Moraxella catarrhalis, Mycobacterium tuberculosis*, and *Candida* spp. including *Candida albicans*.

In various embodiments the microbial disease or disorder is, or the microbial infection is of any one or more of the following microbes: *Aspergillus* spp., including *Aspergillus flavus, Aspergillus fumigatus, Aspergillus niger, Bacillus* spp., including *Bacillus subtilis, Bacillus cereus, Boretella* spp., including *Boretella pertussis, Candida* spp., including *Candida albicans, Candida utilis, Chlamydophila* spp., including *Chlamydophila pneumoniae, Escherichia* spp., including *Escherichia coli, Haemophilus* spp., including *Haemophilus influenzae, Helicobacter* spp., including *Helicobacter pylori, Klebsiella* spp., including *Klebsiella pneumoniae, Listeria* spp., including *Listeria monocytogenes, Micrococcus* spp., including *Micrococcus flavus, Moraxella* spp., including *Moraxella catarrhalis, Mycobacteria* spp., including *Mycobacteria tuberculosis, Mycobacteria paratuberculosis, Mycoplasma* spp., including *Mycoplasma pneumoniae, Pasteurella* spp., including *Pasteurella multocida, Penicillium* spp., including *Penicillium chrysogenum, Proteus* spp., including *Proteus mirabilis* and *Proteus vulgaris, Pseudomonas* spp., including *Pseudomonas aeruginosa/pyocyanea, Salmonella* spp., including *Salmonella typhi, Sarcinalutea* spp., *Serratia* spp., including *Serratia marcescens, Shigella* spp., including *Shigella boydii, Shigella fiexneri*, and *Shigella sonnei, Staphylococcus* spp., including *Staphylococcus albus*, and *Staphylococcus aureus* including methicillin-resistant *Staphylococcus aureus, Streptococcus* spp., including Group B Streptococci, *Streptococcus faecalis, Streptococcus pneumoniae*, and *Streptococcus pyogenes*, and *Vibrio* spp., including *Vibrio cholerae*.

In various embodiments the microbial disease or disorder is, or the fungal infection is of any one or more of the following fungi: *Candida* spp., including *Candida albicans, Candida utilis, Aspergillus* spp., *Penicilliium* spp.

In various embodiments, the microbial disease or disorder is selected from the group comprising burns, venous leg ulcers, leg ulcers of mixed aetiology, diabetic foot ulcers, pressure ulcers, unhealed graft donor sites, abscesses, boils, pilonidal sinuses, infected wounds including those from lower limb surgery, necrotising faciitis, neonatal postoperative wound infection, and gangrene including Fournier's gangrene.

In one embodiment administration of the inventive composition reduces microbial infection, such as bacterial or fungal infection, by 5, 10, 15, 20, 25, 30, 35, 40, 45, 50, 55, 60, 65, 70, 75, 80, 85, 90, 95, 96, 97, 98, 99, or 100%.

In embodiments relating to promoting wound healing, the wound may be selected from the group comprising burns, venous ulcers including venous leg ulcers, leg ulcers of mixed aetiology, diabetic ulcers including diabetic foot ulcers, pressure ulcers, unhealed graft donor sites, abscesses, boils, pilonidal sinuses, cancer wounds, surgical wounds, infected wounds including those resulting from surgery such as lower limb surgery, necrotising faciitis, neonatal postoperative wound infection, and gangrene including Fournier's gangrene.

In one embodiment administration of the inventive composition promotes wound healing (with reference to untreated wound) by 5, 10, 15, 20, 25, 30, 35, 40, 45, 50, 55, 60, 65, 70, 75, 80, 85, 90, 95, 96, 97, 98, 99, or 100%.

Methylglyoxal and Materials Comprising Methylglyoxal

Methylglyoxal (CAS number 78-98-8), also called pyruvaldehyde or 2-oxo-propanal, is the aldehyde form of pyruvic acid. Methylglyoxal is reportedly formed in organisms from several sources: from 3-amino acetone, through lipid peroxidation, and from non-enzymatic dephosphorylation from glyceraldehyde phosphate and dihydroxyacetone phosphate during glycolysis.

Methylglyoxal and materials with methylglyoxal contained in the antimicrobial compositions of this invention are commercially available, eg, Methyglyoxal (Aqueous solution) of Nacalai Tesque Co., Ltd as methylglyoxal, in fermented products like dairy products, beer, wine, roasted coffee and manuka honey as exemplary materials with methylglyoxal contained. Alternatively, methylgloxal or a material with methylglyoxal contained may be prepared independently.

Preferred sources of methylgloxal for use in the invention include methylglyoxal 550 (Manuka Health New Zealand Ltd), manuka honey containing 600 µg/g to 800 µg/g of methylglyoxal and methylglyoxal honey powder mixed with dextrin 50% wt. Those skilled in the art will recognise that other sources may be appropriate, having regard to the teaching herein.

Manuka honey is available from a wide number of sources in New Zealand and elsewhere, commonly as a liquid or creamed form. Preferred sources are those obtained from bee-hives with the resulting honey held in storage, for example to assess the methylglyoxal content. Those skilled in the art will recognise that for use in the present invention, manuka honey may be processed to a form suitable for admixture, for example with cyclodextrin, while maintaining the bioactive ingredients. Typically the manuka honey, or an extract thereof, is processed to a fine particulate form. Various methods of preparing active manuka honey, or an extract thereof, to a particulate form are known. For example, PCT international publication WO 05/120250 discloses a freeze drying method. Fractions can be prepared by using chromatography (such as HPLC) using, for example, a size exclusion matrix or a reverse phase matrix. A typical solvent for use in such processes is water.

In one embodiment the manuka honey is powdered without the addition of any additional compounds.

In an alternate embodiment powdered manuka honey is combined with other compounds that enhance the properties of manuka honey, for example a compound that enhances the ease of formulation or administration, or that enhances antimicrobial activity, or that enhances the stability of one or more antimicrobial activities present in manuka honey. An example of additional compounds are those that improve the therapeutic benefits of the manuka honey. For example, mannitol could be added to enhance the diuretic properties of the resulting composition. Alternatively or additionally other compounds such as excipients, and/or propellants could be added to improve the dosing, manufacturability or delivery properties of the composition.

In particularly contemplated embodiments, the manuka honey, or manuka honey with additional compounds, can be further processed to optimise the drug delivery properties of the resulting composition. For example, the manuka honey powder can be cut to obtain a particle size distribution that enables ready admixture with the other components of the composition, or ease of administration to a subject, etc.

In one embodiment the additional compounds are added prior to powdering, so as to improve the powdering process.

An exemplary process for powdering manuka honey is performed by first heating the honey to kill bacteria, protozoa, yeast, fungi and other organisms that are naturally present in the manuka honey. The honey is then powdered by methods well known in the art. Once powdered, the resulting manuka powder can be stored for admixture, or admixed directly.

It will be appreciated that in certain embodiments of the invention, the material comprising methylglyoxal, such as manuka honey, is admixed with one or more cyclodextrins prior to drying or powderising. Examples of such admixing methods and of the resulting admixtures are presented herein.

Cyclodextrins and Materials Comprising Cyclodextrin

Cyclodextrins are cyclic molecules composed of glucopyranose ring units which form toroidal structures. The interior of the cyclodextrin molecule is hydrophobic and the exterior is hydrophilic, making the cyclodextrin molecule water soluble. The degree of solubility can be altered through substitution of the hydroxyl groups on the exterior of the cyclodextrin. Similarly, the hydrophobicity of the interior can be altered through substitution, though generally the hydrophobic nature of the interior allows accommodation of relatively hydrophobic guests within the cavity. Accommodation of one molecule within another is known as complexation and the resulting product is referred to as an inclusion complex. Cyclodextrins are typically identified with reference to the number of monomeric units that comprise the molecule, wherein alpha-cyclodextrin ($\alpha$-cyclodextrin) comprises six monomeric units, beta-cyclodextrin ($\beta$-cyclodextrin) comprises seven monomeric units, and gamma-cyclodextrin ($\gamma$-cyclodextrin) comprises eight monomeric units. Larger cyclodextrin molecules have been described, including a well-characterised cyclodextrin containing 32 1,4-anhydroglucopyranoside units Cyclodextrin molecules may conveniently be derivatised, by for example chemical modification, for example to alter one or more of the physicochemical properties thereof. Examples of cyclodextrin derivatives include methylated cyclodextrins, sulfobutylcyclodextrin, maltosylcyclodextrin, hydroxypropylcyclodextrin, and salts thereof. Those skilled in the art will recognise that various derivates of cyclodextrin may be suitable for particular purposes, for example, certain derivatives of cyclodextrin may not be acceptable for administration to human subjects, but are suitable for use in compositions of the present invention targeted to industrial uses and applications. In certain embodiments, chemically-modified cyclodextrins are particularly contemplated for such industrial uses and applications.

Cyclodextrins contained in the antimicrobial compositions of the present invention may be commercially available, or may be prepared independently by methods well known to those skilled in the art. It will be apparent to those skilled in the art that cyclodextrins used in the antimicrobial compositions for administration to a subject, for example a cyclodextrin for manufacturing a beverage, food, or pharmaceutical of the invention should be safe to human body, and preferably is a pharmaceutically acceptable cyclodextrin.

Preferably alpha- or gamma-cyclodextrin or combinations thereof are used. In embodiments where alpha-cyclodextrin is used, antimicrobial activity may be especially enhanced, as presented herein in the examples. In embodiments where gamma-cyclodextrin is used, the enhancement in antimicrobial activity may be less pronounced than that by alpha-cyclodextrin. However, compositions comprising gamma-cyclodextrin may provide enhanced mouth feel or palatability, for example compositions comprising gamma-cyclodextrin and manuka honey exhibit a stronger tendency to maintain the sweetness of the manuka honey.

This means that gamma-cyclodextrin may be preferred for use in compositions, such as beverages and foods, in which palatability, and particularly sweet taste, is important.

In case of the antimicrobial compositions for industrial products like as disinfectants for cooling water or washing water in industry, chemically modified cyclodextrins can be used.

Cyclodextrins suitable for use in the present invention can be obtained from commercial sources, or can prepared independently by methods well known in the art, such as from starch by enzymatic conversion. Preferably CAVAMAX W6 Food as alpha-cyclodextrin (CycloChem Co., Ltd.) and CAVAMAX W8 FOOD (CycloChem. Co., Ltd.) as gamma-cyclodextrin are used.

Compositions of the Invention

Exemplary antimicrobial compositions of the present invention include a powder that was spray-dried after mixing methylglyoxal or materials with methylglyoxal contained with cyclodextrin, then adding water and homogenizing the composition. Other exemplary antimicrobial compositions of the present invention include solutions, including for example, those in which methylglyoxal or materials with methylglyoxal contained and cyclodextrin are mixed and then dissolved in water, medium, etc., those in which methylglyoxal or materials with methylglyoxal contained and cyclodextrin are independently dissolved in water, medium, etc. and then admixed, for example kneaded, and further those in which powder prepared as described herein is admixed with cyclodextrin and/or methylglyoxal, then added to water, medium, etc and further mixed, for example kneaded. In certain embodiments, antimicrobial compositions prepared as powders as described above may be preferred, for example because they may maintain stronger antimicrobial activity or may maintain antimicrobial activity for a longer period than that of solutions of antimicrobial compositions prepared as described above.

The content of methylglyoxal or materials with methylglyoxal contained and cyclodextrin of the present invention can be at any level as long as the expected antimicrobial activity is realized, such as from about 0.003% wt to about 0.015% wt of methylglyoxal, or from about 0.006% wt to 0.079% wt of methylglyoxal, 10.0 to 99.0% wt of materials with methylglyoxal contained, eg, manuka honey and 1.0 to 90.0% wt of cyclodextrin. The content can be adjusted by dissolution in or dilution with water, medium, etc. For example, the antimicrobial composition A prepared as the example below utilizes manuka honey as the material with methylglyoxal contained and its concentration is adjusted with water in the example.

Medium prepared so that the concentration of manuka honey can be 7.14% w/v and that of alpha-cyclodextrin can be 8.37% w/v prevented the growth of inoculated *Staphylococcus aureus* more than 96 hours of incubation and is found to be very suited concentration for microbial growth prevention.

In case of the antimicrobial composition B, manuka honey is used as the material with methylglyoxal contained, which is dissolved in water to the intended concentration. Medium prepared so that the concentration of manuka honey can be 3.27% w/v and that of gamma-cyclodextrin can be 4.0% w/v prevented the growth of inoculated *Staphylococcus aureus* more strongly than the concentration of 3.27% w/v of only manuka honey. This means that the concentration was adjusted to the favorable level.

Other antimicrobial substances generally known can be combined with the antimicrobial compositions of this invention, depending upon the application to which the composition is to be put.

Without wishing to be bound by any theory, the applicants believe that the enhanced antimicrobial activity observed in exemplary compositions of the present invention may be due at least in part to a synergy between methylglyoxal, particularly when present as manuka honey, and cyclodextrin, particularly alpha-cyclodextrin and to a lesser extent gamma-cyclodextrin. Again, without wishing to be bound by any theory, the applicants acknowledge that there may be a role of other components of the exemplary compositions, such as polyphenols present in manuka honey, in achieving the observed enhanced antimicrobial activities.

Compositions suitable for administration to a subject may be formulated as a food, drink, food additive, drink additive, dietary supplement, nutritional product, medical food, nutraceutical, medical supply, medical device, medicament or pharmaceutical. Appropriate formulations may be prepared by an art skilled worker with regard to that skill and the teaching of this specification.

In one embodiment the present invention relates to use of methylglyoxl, optionally with at least one antimicrobial agent, in the manufacture of a food, drink, food additive, drink additive, dietary supplement, nutritional product, medical food, nutraceutical, medical device, medical supply, medicament or pharmaceutical. In one embodiment, the composition is formulated for oral administration. In another embodiment, the composition is formulated for parenteral, including topical, administration. Preferably the composition is for inhibiting microbial growth, treating or preventing a microbial disease or disorder, or one or more other uses as described above.

In one embodiment the composition is in the form of a powder, a tablet, a caplet, a pill, a hard or soft capsule or a lozenge.

In one embodiment the composition is in the form of a cachet, a dispensable powder, granules, a suspension, an elixir, a liquid, a drink, or any other form that can be added to food or drink, including for example water or fruit juice. In one embodiment the composition is an enteral product, a solid enteral product or a liquid enteral product.

In one embodiment, the composition is in the form of a cream, ointment, a paste, a drop solution including eye drops or ear drops, an inhaler or as an inhalable composition, a dressing, a pad, or a spray.

In one embodiment the composition further comprises one or more constituents (such as antioxidants) which prevent or reduce degradation of the composition during storage or after administration.

In one embodiment, compositions useful herein include any edible consumer product which is able to carry one or more cyclodextrins. When the composition comprises as the at least one additional antimicrobial agent a proteinaceous factor, the edible consumer product is one able to carry protein. Examples of suitable edible consumer products include baked goods, powders, liquids, confectionary products, reconstituted fruit products, snack bars, food bards muesli bars, spreads, sauces, dips, dairy products including ice creams, yoghurts and cheeses, drinks including dairy and non-dairy based drinks (such as milk drinks including milk shakes, and yogurt drinks), milk powders, sports or nutritional supplements including dairy and non-dairy based sports or nutritional supplements, food additives such as protein sprinkles and dietary supplement products including daily supplement tablets. Within this embodiment, a composition useful herein may also be an infant formula, in powder or liquid form. Suitable nutraceutical compositions useful herein may be provided in similar forms. Particularly contemplated are compositions additionally comprising milk or one or more milk products or components of milk, such as milk protein, whey protein, colostrums, milk fat, or any fractions of milk or one or more milk products or components of milk, such as a milk fat fraction, a milk protein fraction, a whey protein fraction, a colostrums fraction, or the like.

Compositions useful herein may further include other factors such as calcium, zinc, magnesium, selenium, vitamin C, vitamin D, vitamin E, vitamin K2, complex carbohydrates, edible or cooking oils including palm, olive, soybean, canola, corn, sunflower, safflower, peanut, grape seed, sesame, nut, almond, cashew, hazelnut, *macadamia*, pecan, pistachio, and walnut, and other edibles include acai, amaranth, apricot, argan, artichoke, avocado, babassu, ben, blackcurrant seed, borage seed, borneo tallow nut, bottle gourd, buffalo gourd, carob pod (algaroba), cohune, coriander seed, evening primrose, false flax, hemp, kapok seed, lallemantia, meadowfoam seed, mustard, okra seed (hibiscus seed), *perilla* seed, pequi, pine nut, poppyseed, prune kernel, pumpkin seed, quinoa, ramtil, rice bran, tea (camellia), thistle, watermelon seed, or wheat germ oil, or a combination thereof.

The compositions useful herein may be formulated to allow for administration to a subject by any chosen route, including but not limited to oral or parenteral (including topical, subcutaneous, intramuscular and intravenous) administration. Those skilled in the art will appreciate that the route of administration to a subject will typically take into account the purpose for which the composition is being administered—for example, where a pharmaceutical composition of the invention is being administered to treat a microbial disease or disorder, the route of administration will typically be chosen taking into account the nature of the microbial disease or disorder. Accordingly, exemplary compositions for the treatment of skin infections caused by or exacerbated by *Staphylococcus aureus* may be formulated for topical administration.

In general, for oral administration a dietary (a food, food additive or food supplement for example), nutraceutical or pharmaceutical composition useful herein may be formulated by a skilled worker according to known formulation techniques.

Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. See for example, *Remington's Pharmaceutical Sciences*, 16th edition, Osol, A. Ed., Mack Publishing Co., 1980.

While the preferred route of administration is oral, it should be understood that any mode of administration may be suitable for any composition of the invention, including administration by multiple routes, including different routes for different agents. Therefore, inhalation (nasal or buccal inhalation) and vaginal and rectal administration of any composition of the invention is also contemplated. Intramedullar, epidural, intra-articular, and intra-pleural administration of any composition of the invention is also contemplated. Administration of a composition of the invention, optionally with at least one additional antimicrobial factor, by a first administration route accompanied by separate, simultaneous or sequential administration of one or more other agents, including one or more other antimicrobial agents, by a second administration route is also contemplated; for example, oral administration of a composition of the invention accompanied by topical administration of the at least one additional antimicrobial agent.

The compositions of the invention may also be formulated as a dosage form. A dosage form useful herein may be administered orally as a powder, liquid, tablet or capsule. Suitable dosage forms may contain additional agents as required, including emulsifying, antioxidant, flavouring or colouring agents, or have an enteric coating. Suitable enteric coatings are known. Enteric coatings surrounding the active ingredients and prevent the release of the active ingredients in the stomach but allow release after the dosage form has left the stomach. Dosage forms useful herein may be adapted for immediate, delayed, modified, sustained, pulsed or controlled release of the active components. Suitable formulations may contain additional agents as required, including emulsifying, antioxidant, flavouring or colouring agents.

Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Pharmaceutical compositions can also be administered via the parenteral route. Examples of parenteral dosage forms include aqueous solutions, isotonic saline or 5% glucose of the active agent, or other well-known pharmaceutically acceptable excipient. Solubilising agents well-known to those familiar with the art, can be utilized as pharmaceutical excipients for delivery of the antimicrobial agent.

Injectable dosage forms may be formulated as liquid solutions or suspensions. Solid forms suitable for solution in, or suspension in, liquid prior to injection may also be prepared. The dosage form may also be emulsified. Methylglyoxal, or a material comprising methylglyoxal, and cyclodextrin or a material comprising cyclodextrin, and when present the at least one additional antimicrobial factor may be mixed with carriers such as, for example, water, saline, dextrose, glycerol, ethanol, or the like and combinations thereof.

Sustained-release preparations may be prepared incorporating methylglyoxal and cyclodextrin. Suitable examples of sustained-release preparations include semi-permeable matrices of solid hydrophobic polymers containing methylglyoxal and cyclodextrin, and when present the at least one additional antimicrobial agent. The matrices may be in the form of shaped articles, e.g., films, or microcapsules. Examples of sustained-release matrices include polyesters, hydrogels (for example, poly(2-hydroxyethyl-methacrylate), or poly(vinylalcohol)), polylactides (see U.S. Pat. No. 3,773,919), copolymers of L-glutamic acid and ethyl-L-glutamate, non-degradable ethylene-vinyl acetate, and degradable lactic acid-glycolic acid copolymers such as the LUPRON DEPOT™ (injectable microspheres composed of lactic acid-glycolic acid copolymer and leuprolide acetate).

Topical formulations comprising methylglyoxal and cyclodextrin, and when present the at least one additional antimicrobial agent, may be prepared as lotions, creams, ointments, pastes or salves using known carriers for such applications. Such formulations may be administered directly, for example, applied directly on to a wound, sprayed onto a surgical site, etc, or may be applied indirectly, such as by impregnation into a bandage or dressing or sprayed onto surgical equipment, dressings and the like.

The present invention also relates to a parenteral unit dosage form comprising methylglyoxal and cyclodextrin, optionally with at least one additional antimicrobial agent.

In various embodiments, the at least one additional antimicrobial agent is an antibiotic, such as an aminoglycoside, such as amikacin, gentamicin, kanamycin, neomycin, netilmicin, streptomycin, tobramicin, or paromomycin; an ansamycin, such as geldanamycin, or herbimycin; a carbacephem, such as loracarbef; carbapenems, such as, ertapenem, doripenem, imipenem/cilastatin, or meropenem; cephalosporins (first generation), such as cefadroxil, cefazolin, cefalotin or cefalothin, or cefalexin; cephalosporins (second generation), such as cefaclor, cefamandole, cefoxitin, cefprozil, or cefuroxime; cephalosporins (third generation), such as cefixime, cefdinir, cefditoren, cefoperazone, cefotaxime, cefpodoxime, ceftazidime, ceftibuten, ceftizoxime, or ceftriaxone; cephalosporins (fourth generation), such as cefepime; cephalosporins (fifth generation), such as ceftobiprole; glycopeptides, such as teicoplanin, or vancomycin; macrolides, such as azithromycin, clarithromycin, dirithromycin, erythromycin, roxithromycin, troleandomycin, telithromycin, or spectinomycin; monobactams, such as aztreonam; penicillins, such as amoxicillin, ampicillin, azlocillin, carbenicillin, cloxacillin, dicloxacillin, flucloxacillin, mezlocillin, meticillin, nafcillin, oxacillin, penicillin, piperacillin, or ticarcillin; polypeptides, such as bacitracin, colistin, or polymyxin b; quinolones, such as ciprofloxacin, enoxacin, gatifloxacin, levofloxacin, lomefloxacin, moxifloxacin, norfloxacin, or ofloxacin; sulfonamides, such as mafenide, sulfonamidochrysoidine (archaic), sulfacetamide, sulfadiazine, sulfamethizole, sulfanilimide (archaic), sulfasalazine, sulfisoxazole, trimethoprim, or trimethoprim-sulfamethoxazole (co-trimoxazole) (tmp-smx); tetracyclines, such as demeclocycline, doxycycline, minocycline, oxytetracycline, tetracycline; others such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin (rifampin in US), thiamphenicol, tinidazole, dapsone, clofazimine; or a cyclic lipopeptides, such as daptomycin, a glycylcycline, such as tigecycline, or an oxazolidinones, such as linezolid.

In other embodiments, the at least one additional antimicrobial agent is an antifungal, such as a polyene antifungal, such as natamycin, rimocidin, filipin, nystatin, amphotericin B, candicin; imidazoles, such as miconazole, ketoconazole, clotrimazole, econazole, bifonazole, butoconazole, fenticonazole, isoconazole, oxiconazole, sertaconazole, sulconazole, or tioconazole; triazoles, such as fluconazole, itraconazole, isavuconazole, ravuconazole, posaconazole, voriconazole, or terconazole; thiazoles such as abafungin; allylamines, such as terbinafine, amorolfine, naftifine, or butenafine; echinocandins, such as anidulafungin, caspofungin, or micafungin; others such as benzoic acid, ciclopirox, tolnaftate, undecylenic acid, flucytosine or 5-fluorocytosine, griseofulvin, haloprogin, and sodium bicarbonate; or alternatives such as allicin, tea tree oil, citronella oil, iodine, lemon grass, olive leaf, orange oil, palmarosa oil, patchouli, lemon myrtle, neem seed oil, coconut oil, zinc, or selenium Alternatively the agent is selected from any of those described herein.

The efficacy of a composition useful according to the invention can be evaluated both in vitro and in vivo. See, e.g., the examples below. Briefly, in one embodiment the composition can be tested for its ability, to for example, inhibit microbial growth in vitro. For in vivo studies, the composition can be fed to or injected into an animal (e.g., a mouse) and its effects on microbial colonization, infection, or one or more symptoms of the microbial disease or disorder are then assessed. Likewise, the ability of the composition to promote wound healing can be assessed using in vitro models of wound healing, or in vivo. Based on the results, an appropriate dosage range, frequency, and administration route can be determined.

The compositions useful herein may be used alone or in combination with one or more other antimicrobial agents, or one or more additional therapeutic agents. The antimicrobial agent or additional therapeutic agent may be or comprise a food, drink, food additive, drink additive, food component, drink component, dietary supplement, nutritional product, medical food, nutraceutical, medical device, medical supply, medicament or pharmaceutical. The antimicrobial agent or additional therapeutic agent is preferably effective to attenuate one or more microbial diseases or disorders or one or more of the symptoms of one or more microbial diseases or disorders, or otherwise confer a benefit on the subject to whom it is administered. Preferred therapeutic agents include therapeutic food factors, immunogenic or immunostimulatory agents, wound healing agents, and the like.

It should be understood that the additional antimicrobial or therapeutic agents listed above (both food based and pharmaceutical agents) may also be employed in a method according to the invention where they are administered separately, simultaneously or sequentially with a composition useful herein.

As will be appreciated, the dose of the composition administered, the period of administration, and the general administration regime may differ between subjects depending on such variables as the severity of symptoms of a subject, the type of disorder to be treated, the mode of administration chosen, and the age, sex and/or general health of a subject. However, by way of general example, from about 1 mg to about 5000 mg per kg body weight of a composition useful herein is administered, 1 mg to about 4000 mg per kg body weight of a composition useful herein is administered, 1 mg to about 3000 mg per kg body weight of a composition useful herein is administered, 1 mg to about 2000 mg per kg body weight of a composition useful herein is administered, 1 mg to about 1000 mg per kg body weight of a composition useful herein is administered, per administration or per day, preferably about 50 to about 1000 mg per kg, preferably per day. In one embodiment, the administration is of from about 0.05 mg to about 250 mg per kg body weight of a composition useful herein.

In various embodiments, sufficient composition is administered to deliver from about 0.001 mg to about 5 mg of methylglyoxal per kg body weight, from about 0.001 mg to about 4 mg of methylglyoxal per kg body weight, from about 0.001 mg to about 3 mg of methylglyoxal per kg body weight, from about 0.001 mg to about 2 mg of methylglyoxal per kg body weight, from about 0.001 mg to about 1 mg of methylglyoxal per kg body weight, from about 0.001 mg to about 0.5 mg of methylglyoxal per kg body weight, from about 0.001 mg to about 0.1 mg of methylglyoxal per kg body weight, from about 0.001 mg to about 0.05 mg of methylglyoxal per kg body weight, from about 0.001 mg to about 0.01 mg of methylglyoxal per kg body weight, or from about 0.001 mg to about 0.005 mg of methylglyoxal per kg body weight, per administration or per day.

It should be appreciated that administration may include a single dose, such as a single daily dose, or administration of a number of discrete divided doses as may be appropriate. It should be understood that a person of ordinary skill in the art will be able without undue experimentation, having regard to that skill and this disclosure, to determine an effective dosage regime (including dose and timing of administration) for a given condition.

The present invention also relates to a dietary, nutraceutical or oral pharmaceutical composition comprising, consisting essentially of or consisting of methylglyoxal or a material comprising methylglyoxal in combination with cyclodextrin. Preferably the composition consists essentially of about 0.1 to 99 wt methylglyoxal or a material comprising methylglyoxal and about 0.1 to 99 wt cyclodextrin. More preferably the composition consists essentially of about 0.5 to 10 wt methylglyoxal or a material comprising methylglyoxal and about 10 to 99 wt cyclodextrin. Most preferably the composition consists essentially of about 1 wt % methylglyoxal and about 20 wt % cyclodextrin.

In one embodiment a composition of the invention comprises manuka honey or a manuka honey fraction. In one embodiment the composition comprises at least about 1, 5, 10, 15, 20, 25, 30, 35, 40, 45, 50, 55, 60, 65, 70, 75, 80, 85, 90, 95 or 99% by weight manuka honey or a manuka honey fraction, and useful ranges may be selected from any of these values (for example, from about 1 to about 99% by weight, from about 5 to about 99% by weight, from about 10 to about 99% by weight, from about 15 to about 99% by weight, from about 20 to about 99% by weight, from about 25 to about 99% by weight, from about 30 to about 99% by weight, from about 35 to about 99% by weight, from about 40 to about 99% by weight, from about 45 to about 99% by weight, from about 50 to about 99% by weight, from about 55 to about 99% by weight, from about 60 to about 99% by weight, from about 65 to about 99% by weight, from about 70 to about 99% by weight, from about 75 to about 99% by weight, from about 80 to about 99% by weight, from about 85 to about 99% by weight, from about 90 to about 99% by weight, or from about 95 to about 99% by weight).

In one embodiment a composition of the invention comprises cyclodextrin, preferably alpha-cyclodextrin, gamma-cyclodextrin, or both alpha-cyclodextrin and gamma-cyclodextrin. In one embodiment the composition comprises at least about 1, 5, 10, 15, 20, 25, 30, 35, 40, 45, 50, 55, 60, 65, 70, 75, 80, 85, 90, 95 or 99% by weight cyclodextrin, and useful ranges may be selected from any of these values (for example, from about 1 to about 99% by weight, from about 5 to about 99% by weight, from about 10 to about 99% by weight, from about 15 to about 99% by weight, from about 20 to about 99% by weight, from about 25 to about 99% by weight, from about 30 to about 99% by weight, from about 35 to about 99% by weight, from about 40 to about 99% by weight, from about 45 to about 99% by weight, from about 50 to about 99% by weight, from about 55 to about 99% by weight, from about 60 to about 99% by weight, from about 65 to about 99% by weight, from about 70 to about 99% by weight, from about 75 to about 99% by weight, from about 80 to about 99% by weight, from about 85 to about 99% by weight, from about 90 to about 99% by weight, or from about 95 to about 99% by weight).

When used in combination with another antimicrobial agent or therapeutic agent, the administration of a composition useful herein and the other antimicrobial agent or therapeutic agent may be simultaneous or sequential. Simultaneous administration includes the administration of a single dosage form that comprises all components or the administration of separate dosage forms at substantially the same time. Sequential administration includes administration according to different schedules, preferably so that there is an overlap in the periods during which the composition useful herein and other therapeutic agent are provided.

Additionally, it is contemplated that a composition in accordance with the invention may be formulated with additional active ingredients which may be of benefit to a subject in particular instances. For example, therapeutic agents that target the same or different facets of the disease process may be used.

Accordingly, "foods and beverages comprising antimicrobial compositions" of this invention can be used for general foods and health food. Since the antimicrobial compositions of the present invention maintain sweet taste of manuka honey, they can be eaten as they are or in the form of powder like honey or may be used or consumed in the same manner as honey, including being eaten as a spread, for example by spreading them on bread or cracker, or mixing with yogurt, or may be used as a preservative or marinade, for example, as a preservative or marinade for meat. They can be used as an ingredient or raw material for cake, biscuit, cookie, chocolate, sweets and other confectionary, including drops or chewing gum. The compositions of the invention may be added to water as a drink, can be used as sweetener for beverages such as milk, tea, coffee, hot chocolate, etc., and as an ingredient or raw material for fruit juice beverages, sports drink, etc.

"Drugs including antimicrobial compositions" of this invention provide the examples of drugs for the treatment of microbial diseases or conditions, including skin infection, such as that caused by *Staphylococcus aureus* and ones for the prevention or treatment of other conditions such as duodenal ulcer, gastric ulcer, gastric cancer and so caused by *Helicobacter pylori*.

Exemplary drugs of this invention can be administered transdermally or orally so long as the antimicrobial composition is safe to human body.

The compositions of the invention may be or may be incorporated into or onto medical devices and medical supplies. The invention particularly contemplates, but is not limited to, medical devices or supplies used in the treatment of external wounds, surgical wounds, and the like, but those skilled in the art will recognise numerous applications. Exemplary medical devices that are intended as tissue implants include, for example but are not limited to, brachytherapy sources, embolization materials, tumor-bed implants, intra-joint implants, materials to minimize adhesions, and the like. Exemplary stents include, for example but are not limited to, intravascular stents that include for example both balloon-expandable stents and self-expanding stents.

Balloon-expandable stents are available from a number of commercial suppliers, including Cordis. Self-expanding stents are typically composed from a shape memory alloy and are available from suppliers, such as Instent. In the case of stents, a balloon-expandable stent is typically composed of a stainless steel framework or, in the case of self-expanding stents, from nickel/titanium alloy. Exemplary balloons include, for example but are not limited to, balloon catheters including inflatable and self inflatable balloon catheters. The inflatable balloon may be a non-dispensable balloon, typically composed of polyethyleneterephthalate, or it may be an elastic balloon, typically being composed of latex or silicone rubber.

"Medical supplies including antimicrobial compositions" of this invention provide the examples of germicide and disinfectant used for medical devices or facilities. Exemplary medical supplies include dressings, disinfectants, bandages, lavages, and the like.

The medical devices or supplies may be coated or impregnated with compositions of the invention by well recognized methods. One exemplary method of coating a surface of a medical device with the composition of the invention comprises contacting the surface with the composition of the invention so as to cause the surface to be coated with the particular composition of the invention. Coating of the artificial surface may be accomplished using standard methods well known to those of ordinary skill in the art. For example, coating a surface with composition of the invention can be achieved by bathing the artificial surface, either by itself or within a device, in a solution containing the composition of the invention.

Exemplary antimicrobial compositions of the invention, and methods for preparing such compositions will now be described with reference to the following examples.

EXAMPLES

1. Material
   1) manuka honey: Manuaka honey MGO™550 (Manuka Health New Zealand Ltd.)
   2) Methylglyoxal honey powder (Manuka Health New Zealand Ltd.)
   3) Alpha-cyclodextrin: CAVAMAX W6 Food (CycloChem. Co., Ltd.)
   4) Gamma-cyclodextrin: CAVAMAX W8 Food (CycloChem. Co., Ltd.)
2. Manufacturing Method of Antimicrobial Compositions
   Antimicrobial Compositions Containing Manuka Honey

Example 1

Antimicrobial Composition A (Alpha-Cyclodextrin Containing Powder Composition)

Manuka honey was mixed with alpha-cyclodextrin at the ratio of 45.0% wt/55.0% wt and was made to a powder.

60.0 g of manuka honey and 61.3 g of alpha-cyclodextrin were added to 1 L of a beaker, to which 128.7 ml of water was added and the composition was homogenized at 6000 rpm for 5 minutes. After that, water was added so that the solid content was 20.0% wt.

The resultant suspension was spray-dried (drying gas temperature: 160° C.) to obtain powder of Antimicrobial composition A.

Example 2

Antimicrobial Composition B (Gamma-Cyclodextrin Containing Powder Composition)

Manuka honey was mixed with gamma-cyclodextrin at the ratio of 45.0% wt/55.0% wt and was made to a powder (ie, as Antimicrobial composition B) in the same way as that of Antimicrobial composition A as described above as Example 1.

Example 3

Antimicrobial Composition Solution C (Alpha-Cyclodextrin Containing Solution)

14.5454 g of Antimicrobial composition A and 8.0 g of alpha-cyclodextrin were dissolved in water to make 100 mL to produce Antimicrobial composition solution C.

The manuka honey content in Antimicrobial composition solution C (from Antimicrobial composition A) was 6.55% w/v.

Alpha cyclodextrin which came from Antimicrobial composition A, was 8.0% w/v and the separately added alpha-cyclodextrin was 8.0% w/v. Thus total alpha cyclodextrin was 16.0% w/v.

Example 4

Antimicrobial Composition Solution D (Alpha Cyclodextrin—Higher Honey Content)

14.5454 g of Antimicrobial composition A and 6.54 g of manuka honey were dissolved in water to make 100 mL to produce Antimicrobial composition solution D.

Alpha cyclodextrin content in Antimicrobial composition solution D (from Antimicrobial composition A) was 8.0% w/v. Manuka honey which came from Antimicrobial composition A was 6.55% w/v and separately added manuka honey was 6.55% w/v. The total manuka honey content was 13.10% w/v.

Example 5

Antimicrobial Composition Solution E 14.29 g of manuka honey and 17.4 g of alpha-cyclodextrin were dissolved in water to make 100 ml to produce Antimicrobial composition solution E, in which the ratio of manuka honey and alpha-cyclodextrin was 45% to 55% by weight.

Example 6

Antimicrobial Composition Solution F 14.29 g of methylglyoxal honey powder and 17.4 g of alpha-cyclodextrin was dissolved in water to make 100 mL to produce Antimicrobial composition solution F.

Manuka honey content was 14.29% w/v and alpha-cyclodextrin content was 17.4% w/v.

Example 7

Antimicrobial Activity of the Compositions A to F

Compositions A to F were prepared as described in Example 1 to 6 above.

Reagents used were as follows:

(1) Heart infusion broth (Eiken Chemical Co., Ltd.). Bacto™ Heart Infusion Broth (beef heart infusion (from 500 g)-10.0 g, Tryptose-10.0 g, Sodium Chloride-5.0 g/per litre) was prepared according to the manufacturer's instructions.

(2) Methicillin-sensitive *Staphylococcus aureus* MSSA, Strain IFO12732 (Delivered by Kobe Gakuin University) was incubated in heart infusion broth (50 g of beef heart infusion, 1 g of pepton and 0.5 g of sodium chloride per 100 ml) at 37° C. for about 15 hours until OD 600 reached approximately 0.7. This culture was 25 fold diluted and used for measurement.

(3) Samples Prepared Using Compositions A to F of Examples 1 to 6.

Antimicrobial compositions A & B manufactured as shown in Examples 1 and 2 were each dissolved in 100 mL of water so that the concentration could be 29.09% w/v (the concentration of manuka honey and alpha-cyclodextrin was 13.1% w/v, and 15.9% w/v, respectively) and sterilized by filtration with 0.45 μm filter.

The filtrate was diluted with water (1 in 2, 1 in 4, and 1 in 8).

After dilution each filtrate was added to heart infusion broth with the ratio of (1:1). Thus the final concentration of manuka honey and alpha-cyclodextrin or gamma-cyclodextrin in heart infusion broth were as follows:

2 fold (1 in 2) dilution: manuka honey (3.27% w/v), α-cyclodextrin or γ-cyclodextrin (4.0% w/v)
4 fold (1 in 4) dilution: manuka honey (1.64% w/v), α-cyclodextrin or γ-cyclodextrin (2.0% w/v)
8 fold (1 in 8) dilution: manuka honey (0.82% w/v), α-cyclodextrin or γ-cyclodextrin (1.0% w/v).

Antimicrobial composition A (Example 1) was also dissolved in water so that the concentration was 31.75% w/v, (the concentration of manuka honey and α-cyclodextrin was 7.14% w/v, and 8.7% w/v, respectively) and sterilized by filtration with 0.45 μm filter.

The filtrate was added to heart infusion broth with the ratio of (1:1).

Antimicrobial compositions C, D, & E (Examples 3 to 5, respectively) were each sterilized by filtration with 0.45 μm filter.

Each filtrate was added to heart infusion broth with the ratio of (1:1).

4) Reference Samples (a.) Manuka Honey Aqueous Solution 14.29% w/v of manuka honey aqueous solution was prepared by dissolving manuka honey MGO550™ (Cosana Co., Ltd.) with water.

(b.) Cyclodextrin Aqueous Solution

8% w/v of cyclodextrin aqueous solution was prepared by dissolving either CAVAMAXC W6 Food or CAVAMAX W8 Food with water.

(c.) Methylglyoxal Manuka Honey Powder Aqueous Solution 14.29% w/v of manuka honey powder aqueous solution was prepared by dissolving methylglyoxal manuka honey powder (Manuka Health Co., Ltd.) with water.

Solutions a. to c. above were sterilized by filtration with 0.45 μm filter and each filtrate was added to heart infusion broth with the ratio of (1:1).

Measurement of Antimicrobial Activity 5 g of Heart infusion broth and 100 mL of water were added to 200 mL Erlenmeyer flask and sterilized in an autocrave at 120° C. for 20 minutes. To 2 ml of the sterilized medium, 2 ml of either sample or reference sample prepared as above was added. 2 ml of distilled water was added in place of manuka honey aqueous solution as the control.

50 μL of 25-fold diluted strain solution prepared as above was added to each test tube and incubated at 37° C. while shaking.

Optical absorption was measured at 610 nm, and the time of incubation and change in bacterial count was determined.

Results

As shown in FIG. 1, antimicrobial composition A containing 7.14% w/v of manuka honey and 8.7% w/v of alpha-cyclodextrin, and the composition containing 3.27% w/v of manuka honey and 4.0% w/v of alpha-cyclodextrin each showed higher antimicrobial activity than that of manuka honey alone, or alpha-cyclodextrin alone.

Both antimicrobial composition A containing 1.64% w/v of manuka honey and 2.0% w/v of alpha-cyclodextrin, and the composition containing 0.82% w/v of manuka honey and 2.0% w/v of alpha-cyclodextrin, are lower in final manuka honey concentration than was the reference sample of manuka honey alone. Despite this, each showed equivalent antimicrobial activity equivalent to that of the reference sample of manuka honey alone.

Figure 2:
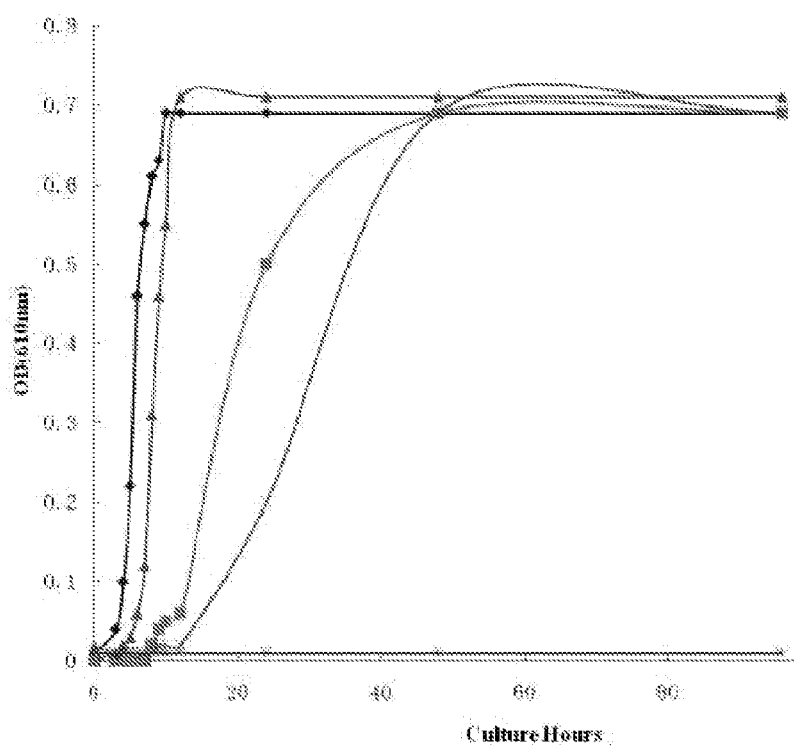
FIG. 2 Antimicrobial activity against *Staphylococcus aureus* of antimicrobial composition A are shown (Test results). ◆ Control; ■ Alpha-CD (4.0 w/v %); ▲ Manuka honey (3.27 w/v %); ><Antimicrobial mixture A (Manuka honey 3.27 w/v %, Alpha-CD 4.0 w/v %); * Antimicrobial mixture A (Manuka honey 7.14 w/v %, Alpha CD8.7 w/v %).

FIG. 2 shows that the high antimicrobial activity of antibacterial composition A, containing 7.14% w/v of manuka honey and 8.7% w/v of alpha-cyclodextrin was maintained to almost 100 hours. FIG. 2 also shows the antimicrobial activity of antimicrobial composition A, containing 3.27% w/v of manuka honey and 4.0% w/v of alpha-cyclodextrin, was maintained for a longer time than that of manuka honey.

Thus, FIGS. 1 and 2 shows that antimicrobial composition A (with manuka honey and alpha-cyclodextrin) showed higher antimicrobial activity than that of manuka honey alone at the same manuka honey concentration. Antimicrobial activity equivalent to that of manuka honey was obtained at a lower manuka honey concentration in those compositions comprising alpha-cyclodextrin.

Figure 3:
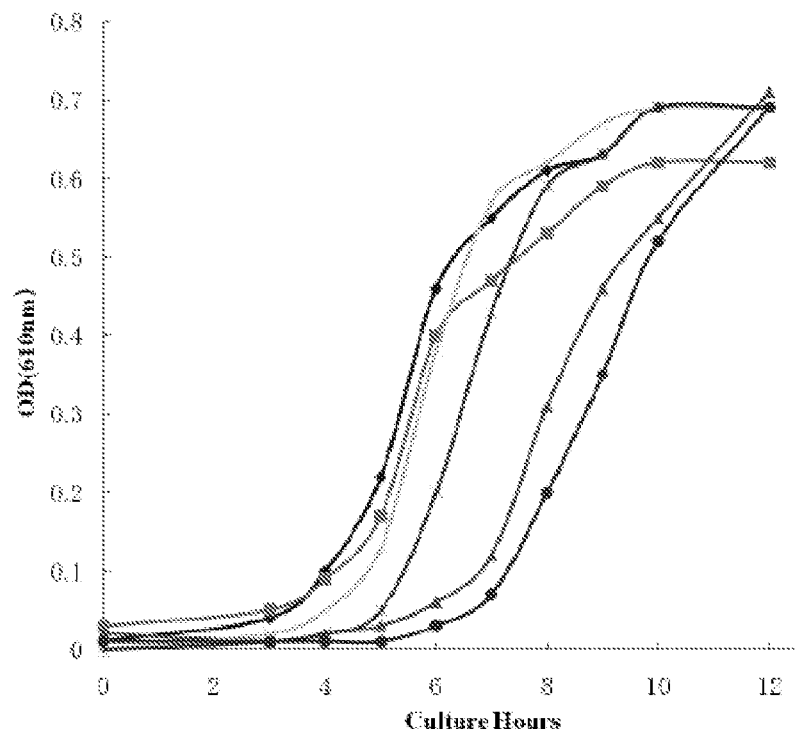
FIG. 3 Antimicrobial activity against *Staphylococcus aureus* of antimicrobial composition B are shown (Test results). ◆ Control; ■ Gamma-CD (4.0 w/v %); ▲ Manuka honey (3.27 w/v %); ><Antimicrobial mixture B (Manuka honey 0.82 w/v %, Gamma-CD1.0 w/v %); * Antimicrobial mixture B (Manuka honey 1.64 w/v %, Gamma-CD2.0 w/v %); ● Antimicrobial mixture B (Manuka honey 3.27 w/v %, Gamma-CD4.0/v %).

FIG. 3 shows that antimicrobial composition B diluted to contain 3.27% w/v of manuka honey and 4.0% w/v of gamma-cyclodextrin exhibited higher antimicrobial activity than that of manuka honey alone.

FIG. 3 also shows that antimicrobial composition B diluted to contain 1.64% w/v of manuka honey and 2.0% w/v of gamma-cyclodextrin, or containing 0.82% w/v manuka honey and 2.0% w/v of gamma-cyclodextrin, showed antimicrobial activity equivalent to that of the manuka honey reference sample at the lower manuka honey concentration.

From the result of FIG. 3, the enhancement of antimicrobial activity of antimicrobial composition B comprising manuka honey and gamma cyclodextrin appears to be dependent on the concentration.

Figure 4:
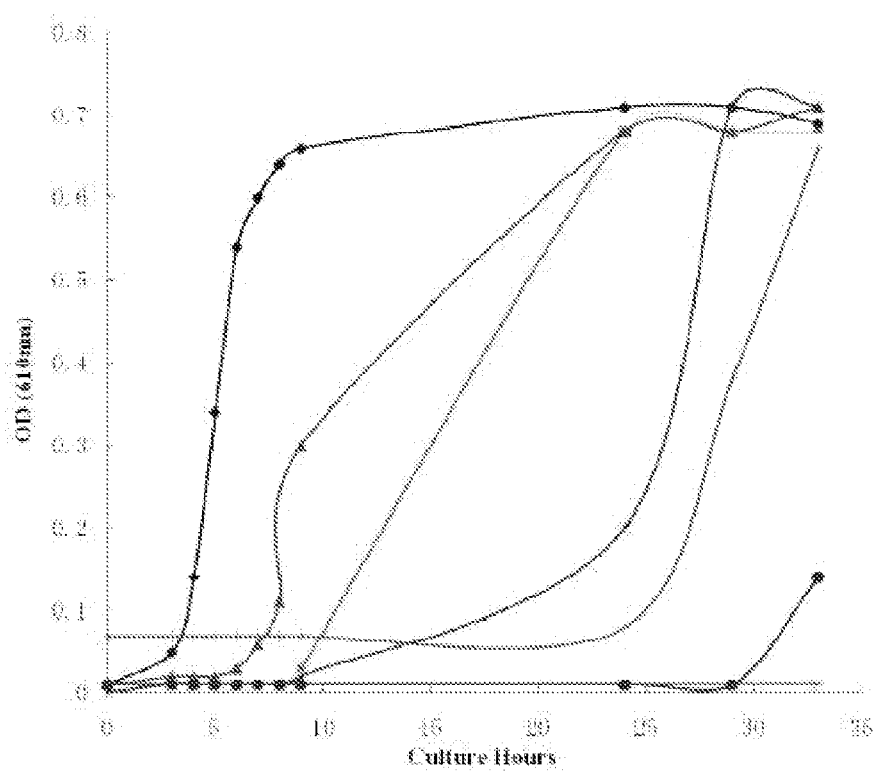
FIG. 4 Antimicrobial activity against *Staphylococcus aureus* of antimicrobial composition A and antimicrobial composition solutions E & F are shown (Test results). ◆ Control; ■ Manuka honey (7.14 w/v %); ▲ MGO Honey power (7.14 w/v %); ><Antimicrobial mixture A (Manuka honey 7.14 w/v %, Alpha CD 8.7 w/v %); * Antimicrobial mixture A (Manuka honey 3.27 w/v %, Alpha-CD4.0 w/v %); ● Antimicrobial mixture solution E (Manuka honey 7.14 w/v %, Alpha-CD8.7 w/v %); +Antimicrobial mixture solution F (MGO Honey 7.14 w/v %, Alpha-CD8, 7 w/v %).

As shown in FIG. 4, antimicrobial composition solution E, in which manuka honey and alpha cyclodextrin were added to the medium at the same concentration of antimicrobial composition A (manuka honey: 7.14% w/v and alpha-cyclodextrin: 8.7% w/v), showed high antimicrobial activity. However, the antimicrobial activity of antimicrobial composition solution E diminished after more than 28 hours. This suggests that antimicrobial composition A which was powderized beforehand possessed longer-lasting enhancement of antimicrobial activity.

Also, antimicrobial composition solution F containing 7.14% w/v of methylglyoxal honey powder and 8.7% w/v of alpha-cyclodextrin was shown to have high antimicrobial activity, though that activity was lower than that of antimicrobial composition A containing the same concentration of manuka honey and alpha-cyclodextrin.

Figure 5:
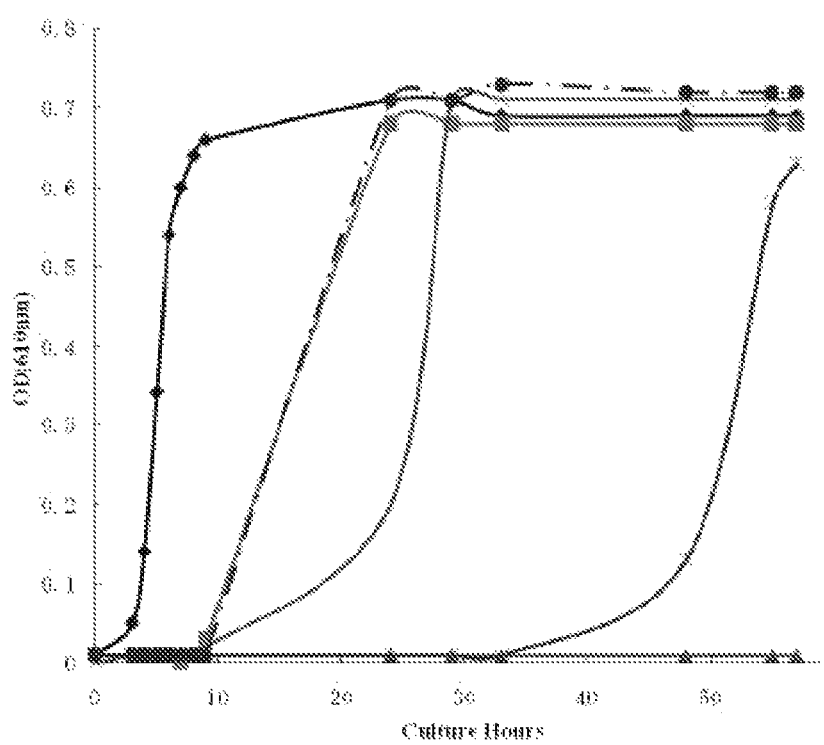
FIG. 5 Antimicrobial activity against *Staphylococcus aureus* of antimicrobial compositions A and antimicrobial composition solutions C & D are shown (Test results). ◆ Control; ■ Manuka honey (7.14 w/v %); ▲ Antimicrobial mixture A (Manuka honey 7.14 w/v %, Alpha-CD8, 7 w/v %); ><Antimicrobial mixture A (Manuka honey 3.27 w/v %, Alpha-CD4.0 w/v %); * Antimicrobial mixture solution C (Manuka honey 3.27 w/v %, Alpha-CD4.0 w/v %)+α CD4.0 w/v %; ● Antimicrobial mixture solution D (Manuka honey 3.27 w/v %, Alpha-CD4.0 w/v %)+Manuka honey 3.27 w/v %.

As shown in FIG. 5, high antimicrobial activity of antimicrobial composition A containing 7.14% w/v of manuka honey and 8.7% w/v of alpha-cyclodextrin lasted almost 60 hours. Further, antimicrobial composition solution C which was manufactured in the similar way as that of antimicrobial composition A with additional alpha cyclodextrin showed high antimicrobial activity.

Also, antimicrobial composition solution D which was manufactured in the similar way as that of antimicrobial composition A with additional manuka honey also showed high antimicrobial activity.

Industrial Applicability

Antimicrobial compositions of this invention containing methylglyoxal or material with a methylglyoxal presence are capable of maintaining or enhancing the original antimicrobial activity present, and can be used in a variety of applications where antimicrobial activity is desired, such as in materials for consumer goods including foods and beverages, medical devices, medical supplies, pharmaceuticals, functional foods, drugs, or in industrial products. Methods of preparing such compositions, and methods of using such compositions, for example in the treatment of microbial disease or in promoting wound healing, have application in the medical and industrial fields.

The invention claimed is:

1. A method of promoting wound healing, the method comprising administering to a subject in need thereof a composition comprising honey from *Leptospermum* species and cyclodextrin.

2. The method according to claim 1 wherein the honey from *Leptospermum* species is manuka honey.

3. The method according to claim 1 wherein the composition is directly applied to the wound.

4. The method according to claim 1 wherein the composition is applied to the wound, by application to bandages, dressings, solutions, or surgical equipment.

5. The method according to claim 1 wherein the honey has a methylglyoxal concentration of greater than about 30 mg/kg, than about 38 mg/kg, than about 40 mg/kg, about 50 mg/kg, about 60 mg/kg, about 70 mg/kg, about 80 mg/kg, about 90 mg/kg, about 100 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg, about 750 mg/kg, about 800 mg/kg, about 850 mg/kg, about 900 mg/kg, about 950 mg/kg, greater than about 1000mg/kg, greater than about 1100 mg/kg, greater than about 1200mg/kg, greater than about 1300mg/kg, greater than about 1400 mg/kg, greater than about 1500 mg/kg, greater than about 1600 mg/kg, greater than about 1700 mg/kg, greater than about 1800 mg/kg, greater than about 1900 mg/kg, or about 2000 mg/kg.

6. The method according to claim 1 wherein the honey has an non-peroxide activity rating greater than 10, than 15, than 20, than 25, 26, 27, 28, 29, 30, than 31, 32, 33, 34, or greater than 35.

7. The method according to claim 1 wherein the cyclodextrin is alpha-cyclodextrin.

8. The method according to claim 1 wherein the cyclodextrin is gamma-cyclodextrin.

9. The method according to claim 1 wherein the cyclodextrin is a combination of alpha-cyclodextrin and gamma-cyclodextrin.

10. The method according to claim 1 wherein the honey content is within the range of about 10.0 to about 99.0% wt.

11. The method according to claim 1 wherein the methylglyoxal content of the antimicrobial composition is within the range of about 0.003% wt to about 0.15% wt.

* * * * *

UNITED STATES PATENT AND TRADEMARK OFFICE
CERTIFICATE OF CORRECTION

PATENT NO. : 8,679,527 B2  
APPLICATION NO. : 13/124101  
DATED : March 25, 2014  
INVENTOR(S) : Keiji et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 230 days.

Signed and Sealed this

Twenty-ninth Day of September, 2015

Michelle K. Lee
*Director of the United States Patent and Trademark Office*